United States Patent [19]
Cathcart et al.

[11] Patent Number: 5,681,347
[45] Date of Patent: Oct. 28, 1997

[54] VENA CAVA FILTER DELIVERY SYSTEM

[75] Inventors: Bruce C. Cathcart, Westerly, R.I.; Robert B. DeVries, Marlborough; Kathleen A. Vigue, Needham, both of Mass.

[73] Assignee: Boston Scientific Corporation, Natick, Mass.

[21] Appl. No.: 447,457

[22] Filed: May 23, 1995

[51] Int. Cl.$^6$ ............................................. A61M 29/00
[52] U.S. Cl. ........................ 606/200; 604/107; 604/280
[58] Field of Search .................................. 604/104–107, 604/280; 606/191, 198, 200, 108

[56] References Cited

U.S. PATENT DOCUMENTS

| | | | |
|---|---|---|---|
| 3,952,747 | 4/1976 | Kimmell, Jr. | 128/303 |
| 4,425,908 | 1/1984 | Simon | 128/1 |
| 4,590,938 | 5/1986 | Segura et al. | 128/328 |
| 4,611,594 | 9/1986 | Grayhack et al. | 128/328 |
| 4,793,348 | 12/1988 | Palmaz | 128/325 |
| 4,817,600 | 4/1989 | Herms et al. | 128/303 |
| 4,832,055 | 5/1989 | Palestrant | 128/899 |
| 4,922,905 | 5/1990 | Strecker | 606/195 |
| 4,950,227 | 8/1990 | Savin et al. | 604/8 |
| 5,059,205 | 10/1991 | El-Nounou et al. | 606/202 |
| 5,300,086 | 4/1994 | Gory et al. | 606/200 |

*Primary Examiner*—Corrine M. McDermott
*Attorney, Agent, or Firm*—Pearson & Pearson

[57] ABSTRACT

A delivery system for delivery and deployment of devices having abrading portions within a patient's lumen. A lumen in a flexible catheter that extends proximally from a distal end of the catheter receives the device in a compact form. At least one impervious segment positioned in the lumen overlies the abrading portions of the device to shield and buffer the surface of the lumen from the abrading portions. The segment is of a relatively short length so that the catheter remains relatively flexible therealong to enable relative ease in the transit of the catheter through the patient's lumen to a delivery site. Additional segments may be disposed in the catheter distally of the segment or the segment may move with the device to the distal end to buffer the walls of the catheter during the deployment of the device. Additional segments mate with the segment so that engaged ones of the segments are relatively radial deflectable.

30 Claims, 5 Drawing Sheets

VENA CAVA FILTER DELIVERY SYSTEM

BACKGROUND OF THE INVENTION

1. Field of the Invention

This invention relates to vena cava filters and like devices and more particularly to delivery systems for such devices.

2. Description of Related Art

A vena cava filter is one species of expansible devices that can be inserted percutaneously into a human. Stents, retrieval baskets and grasping devices constitute other species of such expansible devices. A delivery system generally transports such a device in a compact form to a placement site in a particular vessel. Manipulation of controls associated with the delivery system causes or enables the device to expand into a final configuration within the vessel. Although delivery system will have the foregoing characteristics in common, any delivery systems for a specific device will have particular features for optimizing its operation with a specific device.

For example medical stents, as known, serve as prothesses and graft carriers during percutaneous angioplasty procedures. Corresponding stent delivery systems generally include catheters with selectively expansible devices to deliver and either expand a compacted stent or allow the stent to expand. The following patents disclose such stent delivery systems.

U.S. Pat. No. 4,922,905 (1990) Strecker
U.S. Pat. No. 4,950,227 (1990) Savin et al.

In Strecker a tubular stent comprises knitted metal or plastic filaments. The delivery system includes a balloon catheter and a coaxial, radially flexible sheath for overlying the stent in a compact form carried on the balloon. The catheter supports and carries the compacted stent to a placement. The sheath inhibits premature deployment and facilitates transit of the stent during insertion. After moving the sheath axially with respect to the catheter, expansion of the balloon enlarges the stent and urges it into contact with surrounding vessel walls. Deflation of the balloon frees it from the stent and enables withdrawal of the delivery system from the patient.

Savin et al. also disclose a delivery system with a catheter having an expansible distal portion that carries a stent in its compacted configuration. An axially flexible sleeve overlies portions of the stent and slides axially away from the stent in response to expansion of an expansible portion of the system underlying the stent and consequential expansion of the stent. The sleeve protects the vessel and the stent during insertion without substantially inhibiting deployment of the stent.

The following United States Letters Patents describe various types of systems for the percutaneous insertion of grasping devices, such as retrieval baskets:

U.S. Pat. No. 4,590,938 (1986) Segura et al.
U.S. Pat. No. 4,611,594 (1986) Grayhack et al.

Segura et al. disclose a delivery system for a retrieval basket for stones and the like from the kidneys, the ureter or the biliary duct. The delivery system comprises an elongated tube generally inserted through the working channel of an endoscope. A physician selectively positions the retrieval basket that is in a compact condition within a distal end of the tube. Then the physician extends the basket from the distal end of the tube so it expands into a bulbous shape. In one embodiment the tube includes an inner wire coil that surrounds the basket in its compact form. The coil provides flexibility and strength at the distal end.

Grayhack et al. disclose another system for a delivery and deployment with an elongated smooth outer tubular sheath overlying and containing a stranded wire cable terminating in a distal protective tip at the working or distal end of the device. When a user distally extends the cable, the individual spring wire strands at the distal end expand to form a retrieval basket. Retraction of the cable into the tube returns the distal end of the cable to its compact form. The catheter portion surrounding the retrieval basket in its retracted and compact state comprises an expandable distal end that facilitates the capture of a stone.

Vena cava filters differ from stents and retrieval baskets primarily because vena cava filers include legs that terminate in pointed, outwardly facing hooks. Typically vena cava filters are expanded in a free state. Consequently when a vena cava filter is constrained in its compact configuration, internal stresses urge the free ends of the hooks radially outward and attempts to drive the hooks into any constraining member. As will be apparent, the delivery systems in the foregoing patents are not adapted for delivery vena cava filers because the hooks will penetrate surrounding tubing, catch between adjacent coil turns or otherwise become fixed in the distal end. The occurrence of any of these conditions can increase the complexity of the procedure or render the instrument completely useless. Consequently special delivery systems or vena cava filters formed of special materials or in special shapes have been used for the percutaneous insertion of vena cava filters, such as disclosed in the following patents:

U.S. Pat. No. 3,952,747 (1976) Kimmell, Jr.
U.S. Pat. No. 4,425,908 (1984) Simon
U.S. Pat. No. 4,793,348 (1988) Palmaz
U.S. Pat. No. 4,817,600 (1989) Herms et al.
U.S. Pat. No. 4,832,055 (1989) Palestrant
U.S. Pat. No. 5,300,086 (1994) Gory et al.

Kimmell, Jr. discloses a delivery system with an elongated metal carrier disposed at the distal end of a catheter. The filter overlies the carrier and a locking collar overlies the hooks to retain the legs against the carrier in a compact configuration. Actuating a syringe increases the pressure on a piston in the carrier to drive a distal portion of the carrier and the filter distally with respect to the delivery system whereby the hooks move away from the locking collar and expand into contact with the walls of the vessel.

Simon discloses a system for delivering a Nitinol wire vena cava filter. The filter is formed along an axis and has a low temperature compact shape in which the legs cross the axis so the hooks extend upwardly toward the axis and do not engage the delivery system. Upon warming in the lumen at the delivery site the filter expands into its desired shape whereby the hooks penetrate and lock into the surrounding vessel. The delivery system includes apparatus for providing a cold infusion drip for maintaining a cool temperature in the catheter during the positioning of the filter.

In Palmaz a vena cava filter comprises a material which has essentially no expansion forces in its compacted form but will lock into and expanded position. A balloon expands the filter after a sheath is removed. As there are no internal forces, the hooks do not penetrate the walls of the delivery system during transport.

Herms et al. disclose a delivery system with a first outer catheter and an overlying sheath that are positioned with their respective distal ends proximate a delivery site. An insertion catheter carries a cartridge with a filter in a compact form and positioned with the hooks at the distal end. The hooks do not tend to embed in the catheter wall and can move distally with respect to the cartridge. This delivery system is useful in therapies where apex of the filter points proximally of the hooks, typically upstream with respect to blood flow.

Palestrant discloses, in one embodiment, a system in which a catheter tube is prepositioned in a patient. Then the filter is pushed through the entire length of the catheter with the legs compressed into a compact form. The filter has two portions including a distal portion that expands to form a mesh as two spaced connections are drawn together. The leg portions extend proximally from one connector and spring into an open or expanded position when they exit the distal end of the catheter.

Gory et al. discloses a catheter delivery system for deploying a reversible vena cava filter. The legs of the vena cava filter parallel or converge on the catheter axis so the ends of the filter legs do not snag or catch an inner catheter surface. This allows the vena cava filter to be inserted relatively simply.

Figure 1:
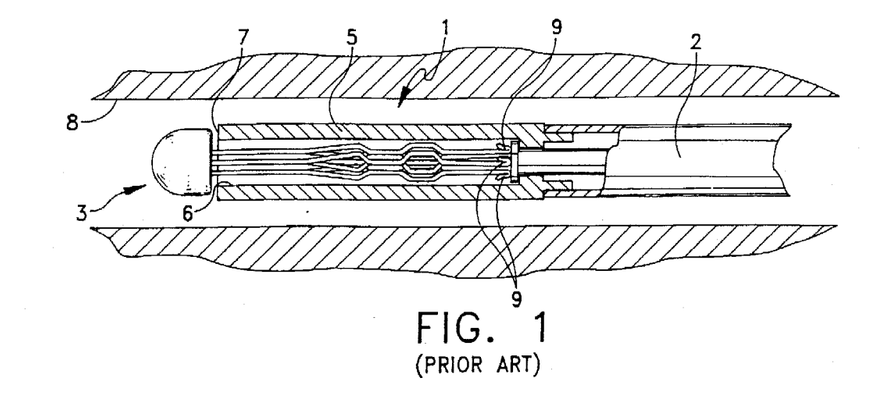
FIG. 1 is an enlarged view, partially in cross section, of a distal end portion of a prior art delivery system.

FIG. 1 depicts another embodiment of a prior art delivery system 1 for use with a long, radially flexible tube 2 that houses a self-expansible vena cava filter 3 in a compact form in a defined cavity 6 of a coaxial metal tube or sleeve 5 that extends from the distal end of the tube 2. The sleeve thus overlies the filter 3 within the defined cavity 6. Manipulation of a slide portion (not shown) displaces the filter 3 distally relative to the sleeve 5 and the tube 2 to urge the filter 3 through a distal end 7 into a patient's lumen 8. A previously positioned guidewire (not shown) is generally used to position the distal end of the delivery system at the delivery site. The sleeve 5 is formed of a material that hooks 9 at the end of the vena cava filter 3 can not perforate or otherwise penetrate during insertion or deployment of the vena cava filter 3.

The foregoing delivery systems generally effectively and reliably deploy vena cava filters carried within the sleeve. However, their use can be limited, as for example, by the inflexibility of the sleeve of the delivery system of FIG. 1 and hence of the distal end of the tube, that makes it difficult to negotiate tortuous paths frequently encountered during a percutaneous insertion. If a physician discovers such a tortuous path, the physician may be forced to discontinue the procedure and elect an alternative procedure, such as major surgery with its additional risks and trauma to a patient. Alternatively, the physician may elect to force the distal end along such path, notwithstanding possible damage to vessels, "kinking" of the distal end or both. "Kinking" can permanently deform or bend the surrounding sleeve and further complicate navigation of the distal end. "Kinking" can also cause the tube essentially to double over proximally of the sleeve. "Kinking" both further complicates the procedure and increases the time necessary to perform the procedure.

Collectively the prior art delivery systems may require a specially formed filter, may require pushing implements to displace a vena cava filter through portions or the entire length of a catheter. For example, Gory et al. require the use of a vena cava filter that does not include sharp hooks that can penetrate or abrade a surrounding sleeve. Simon is limited to a vena cava filter formed of a two-phase material so that the hooks thereof do not imbed in the walls of the catheter prior to delivery thereof. The vena cava filters disclosed by Simon and Palestrant must be pushed through a catheter from the proximal to the distal end. Palmaz uses a special vena cava filter structure that locks in an expanded shape after inflating a balloon. Palestrant discloses a vena cava filter located in the distal end of a catheter, but in the apparatus an outer catheter must be prepositioned.

The prior art thus fails to provide a delivery system simply manufactured, simply used, reliable system for efficiently transporting through and deploying in a patient's lumen a self-expanding vena cava filter having radially extending hook portions that contact the walls of the delivery system. The prior art also fails to provide a delivery system that transports such a vena cava filters within a distal end section to enable relatively immediate delivery of the vena cava filter while enabling radial flexion of the distal end section. The delivery systems of the prior art also fail to imperviously encase radially extending abrading portions of such devices while enabling relatively free radial deflection along the delivery system contiguous with the device.

SUMMARY

Therefore it is an object of this invention to provide an improved delivery system for percutaneous insertion of an expansible device, such as a vena cava filter.

It is another object of this invention to provide a delivery system for transporting an expansible device to a deployment site at the distal end of the system while maintaining radial flexibility at the distal end.

It is yet another object of this invention to provide a delivery system having a segmented housing at a distal end of a catheter for constraining an expansible vena cava filter during delivery to a deployment site.

It is a further object of this invention to provide a delivery system for reliably deploying a self-expanding vena cava filter while maintaining radial flexibility of the distal end during insertion.

According to one aspect of this invention a delivery system deploys a percutaneously inserted self-expanding vena cava filter in a patients lumen the system includes an elongated, radially flexible and axially stiff tubular member extending proximately from a distal end and having a distal end section that constrains the self-expanding filter in a compact condition during transport to a deployment site. Control apparatus is provided for deploying the filter with the improvement comprising a segment carried in the distal end of the tubular member and in between the tubular member and the filter. The segment is relatively short compared to the actual extension of the filter with an inner surface that is a penetration resistent to the filter such to that the segment protects the tubular member from damage during transport of the filter.

According to another aspect of this invention a delivery system delivers a self-expanding vena cava filter in a compact form as a delivery site in a patient's lumen and for selective deployment in an expanded form thereat. The system includes a flexible catheter with an internal lumen for receiving and housing the filter and extending proximally from a distal end for insertion into and transport along a patients lumens to a delivery site. A retainer carried in the catheter's lumen overlies the penetrating portions of the filter when housed in the lumen to shield the catheter from the exposed penetrating portion and enabling a radially flexion of the catheter therealong. Controls at the proximal end of the system distally enable selective deployment of the filter into the lumens of a patient.

According to a further aspect of this invention a method for delivering a self-expanding vena cava filter with a radially extending penetrating portion includes positioning the vena cava filter in a distal section of a radially flexible, axially stiff elongated tube. The distal section of the tube is urged through a patient's lumen to a delivery site with an impervious, relatively short sheath segment interposed between the penetrating portion and the tube during the urging step with the distal end section remaining relatively radially flexible. The filter is then urged distally relative to the tube through an aperture to thereby deploy the filter at the delivery site.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 2:
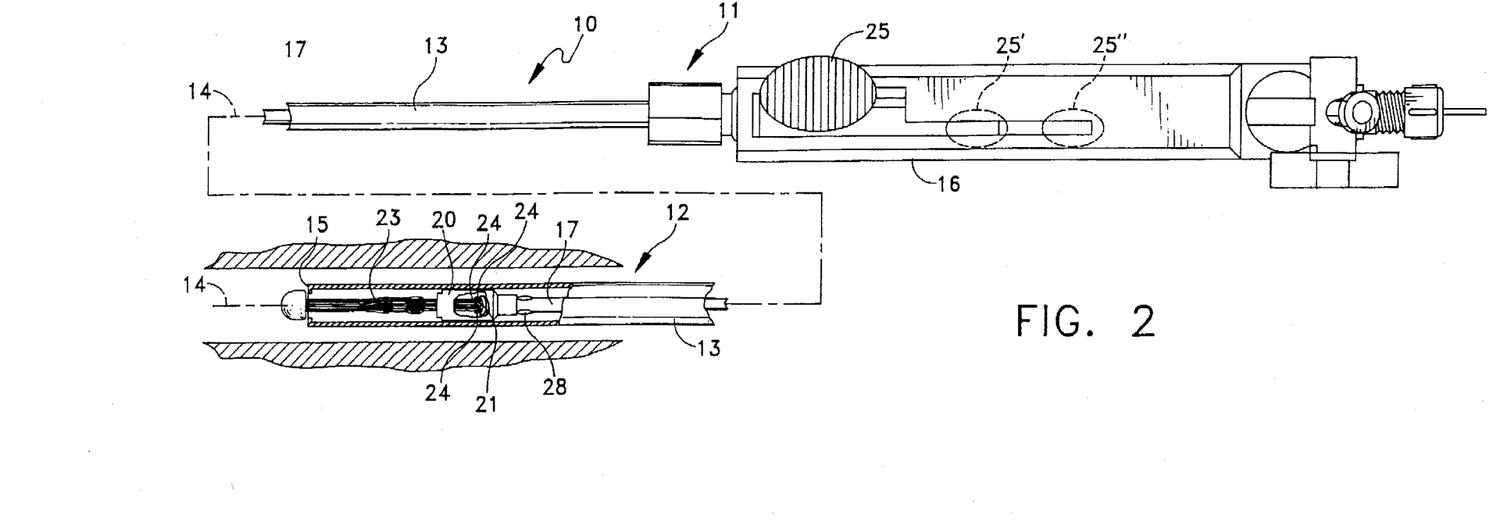
FIG. 2 is a plan view of a delivery system, partially in cross-section constructed in accordance with this invention with a handle at a proximal end and a compact vena cava filter in a distal end portion.

A delivery system 10 according to this invention as depicted in FIG. 2 comprises a proximal base 11 suited for positioning exteriorly of a patient and a distal portion 12 for insertion into a patient. The distal portion 12 includes an outer tubular member 13 proximally extending along an axis 14 from a distal end 15 of the system 10 to a handle 16 of the proximal base 11, an inner member 17 co-axially underlying the outer member 13 and extending distally from the handle 16, and a metal tubular segment 20. The metal segment 20 has a substantially smooth inner bore.

Figure 3:
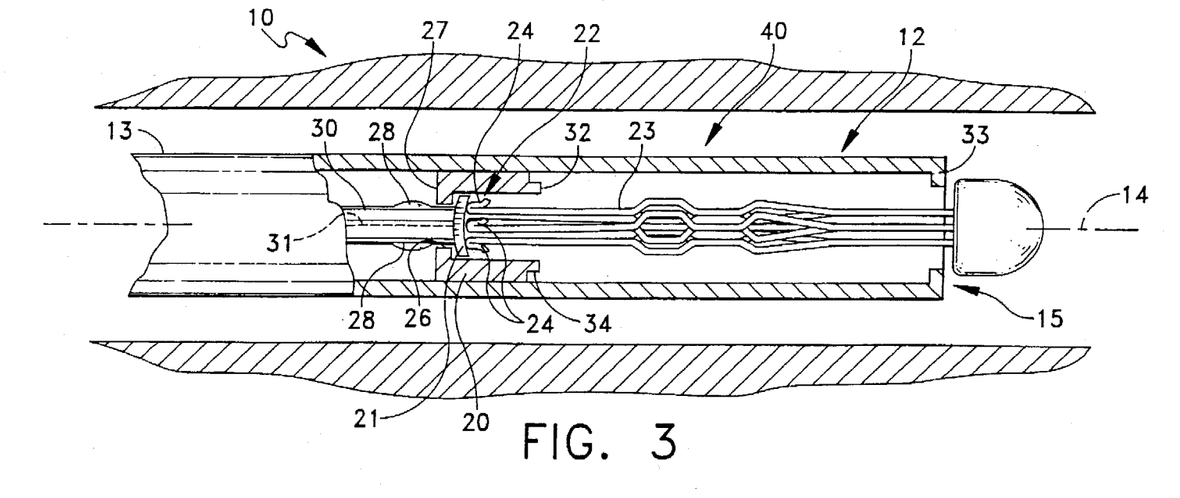
FIG. 3 is a enlarged plan view, partially in cross section, of the distal end portion of FIG. 2.

Referring to FIG. 3, a cup shaped portion 21 engages a proximal end 22 of a device 23, such as a vena cava filter, having radially extending penetrating or hook portions 24 disposed within the inner portion of the metal segment 20. The remainder of the filter 23 extends distally therefrom in the distal portion 12 of the delivery system 10 with a portion extending beyond the distal end 15. Displacement of the inner member 17 distally relative to the outer member 13 moves the cup shaped portion 21 from the first position depicted in FIG. 3 through a second position depicted in FIG. 4 to a third position depicted in FIG. 5 in which the cup shaped portion 21 distally extends beyond the distal end 15, and the filter 23 deploys in a patient's lumen.

Control of the relative distal displacement of the filter 23 to enable selective deployment thereof comprises control apparatus that includes a slider 25 shown in FIG. 2 disposed in the handle 16 for manual manipulation by a user of the delivery system 10. Preferably the slider 25 connects with the outer tubular member 13 in a known manner so that proximal displacement of the slider 25 retracts the outer tubular member 13 relative to the handle 16 and the inner member 17 secured to the handle 16. Thus, the positions of the slider 25 (i.e., the depicted positions 25, 25' and 25" of the slider in FIG. 2) correspond with the positions of the inner member 17 in FIGS. 3, 4, and 5, respectively. Alternatively, the slider 25 could be connected to the inner member 17 with the outer tubular member 13 fixed to the handle 16 so that distal movement from the proximal position 25" to the position 25 of FIG. 2 displaces the inner member 17 distally relative to the handle and the tubular member secured thereto. In either case, the movement of the slider 25 causes the deployment of the filter 23 from the distal end 15 of the system 10. Thus, the control apparatus can be in a general sense considered to include the outer tubular member 13, the handle 16, the inner member 17 and the slider 25.

Figure 4:
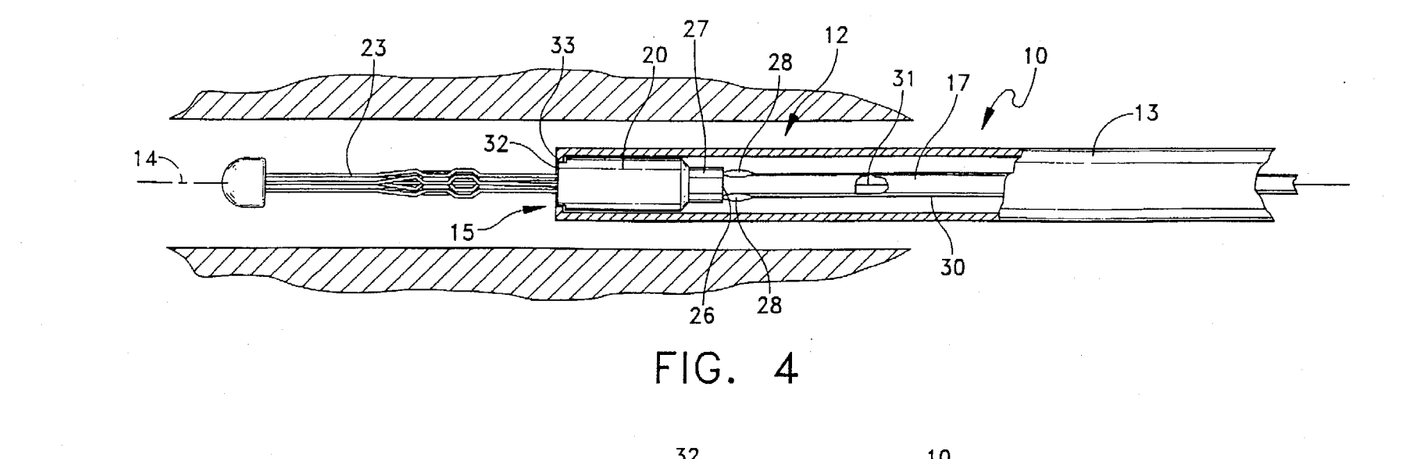
FIG. 4 is a enlarged plan view, partially in cross section, view of the distal end portion of FIG. 2 with the vena cava filter partially deployed therefrom.
Figure 5:
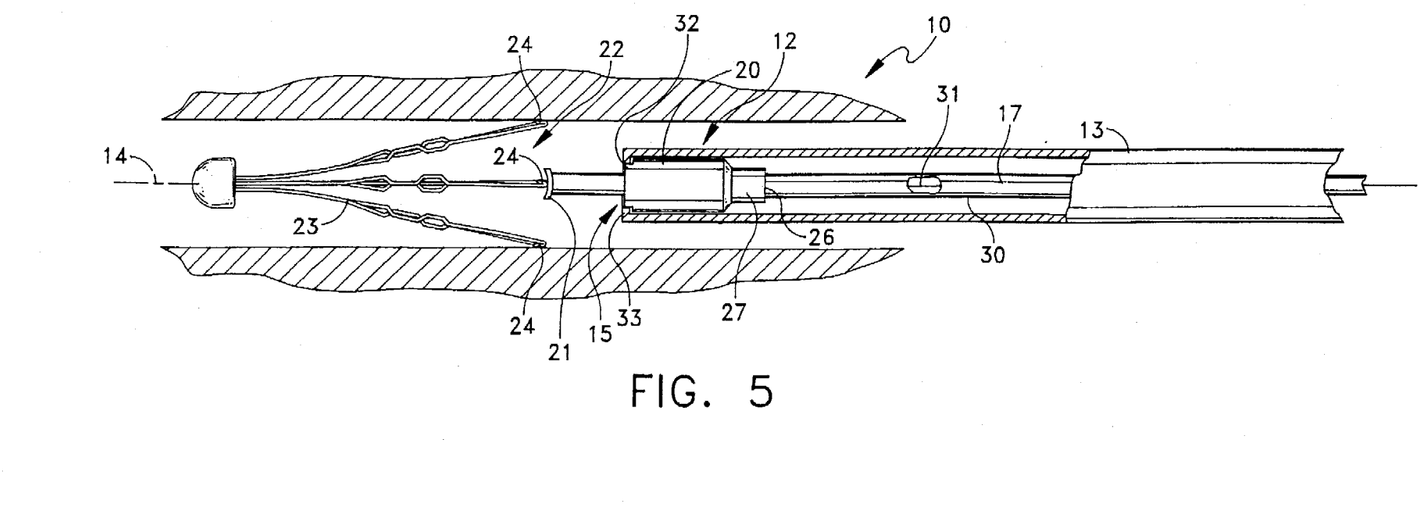
FIG. 5 is an enlarged plan view of the distal end portion of FIGS. 2 with the vena cava filter deployed in a patient's lumen.

Referring now to FIGS. 3 through 5, the inner member 17 extends through an aperture 26 in the proximal end 27 of the metal segment 20 with the cup shaped portion 21 and radially extending tabs 28 disposed on opposed sides of the aperture 26. The inner member 17 in this embodiment comprises an axially stiff, radially flexible member 30, such as a thin stainless steel cable or a suitable polymeric material with the cup shaped portion 21 formed at the distal end thereof. It is preferred that the member 30 is hollow to receive a member such as a guidewire 31 which can pass through an aperture (not shown) in the cup shaped member, between the legs of the filter 23 and through an aperture (not shown) in the distal end of the filter 23. The cup shaped portion 21 engages the base end of the filter 23 for retaining it and thereby to enable the deployment of the device 23. As the outer tubular member 13 initially moves proximally relative to the inner member 17, the metal segment 20 is retained stationary relative to the inner member 17 between the cup shaped portion 21 and the tabs 28 until the distal or leading edge 32 of the metal segment 20 engages a stop 33 formed at the distal end 15 of the outer tubular member 13 as depicted in FIG. 4.

The stop 33 in this instance is a reduced inner diameter portion formed at the distal end 15 of the outer tubular member 13 that engages a mating surface 34 formed on the distal or leading edge 32 of the metal segment 20. The mating surface 34 comprises a reduced outer diameter portion at its distal end 32 compared to the remainder of the metal segment 20. The outer mating surface 34 could take a variety of shapes including a tapered shape. This relationship between the stop 33 and the mating surface 34 enables the distal most end of the metal segment to extend into the aperture defined by the stop 33 at the distal end 15 of the outer tubular member 13 during the distal displacement of the metal segment 20 relative to the outer tubular member 13 and for the surface of the aperture 26 in the proximal portion 27 of the metal segment 20 to bear upon the tabs 28 with continued urging of the slider 25 after engagement of the stop 33 and the metal segment 20.

Relative proximal displacement of the outer tubular member 13 to the inner member 17 upon engagement of the leading edge 32 with the stop 33 thus causes the surface of the aperture 26 of the metal segment 20 to bear on the tabs 28. The tabs 28 consequently deflect to enable distal movement of the inner member 17 relative to both the metal segment 20 and the outer tubular member 13. Thus, once the metal segment 20 and the stop 33 engage, the continued relative proximal displacement of the outer tubular member 13 relative to the filter 23 causes the deployment of the filter 23 from the distal end 15 with the cup shaped member 21 moving through the metal segment 20 to the position depicted in FIG. 5.

After deployment of the filter 23, the delivery system 10 is withdrawn by retracting the outer tubular member 13 either along the guidewire, if it remains so positioned, or merely along the path defined by the outer tubular member 13. The relatively short length metal segment 20 and the stop 33 after the engagement thereof during deployment of the filter 23 ordinarily will not require disengagement for withdrawing the system. That is, the flexibility of the distal end 15 of the outer tubular member 13 is not significantly changed by the engagement or disengagement of the metal segment 20 and the stop 33. Nevertheless, displacement of the slider 25 in the opposite manner to deployment of the filter 23 causes the cup shaped member 21 to bear on the metal segment and displace it proximally relative to the outer tubular member 13 and thereby disengage the stop 33 and the metal segment 20.

Figure 6:
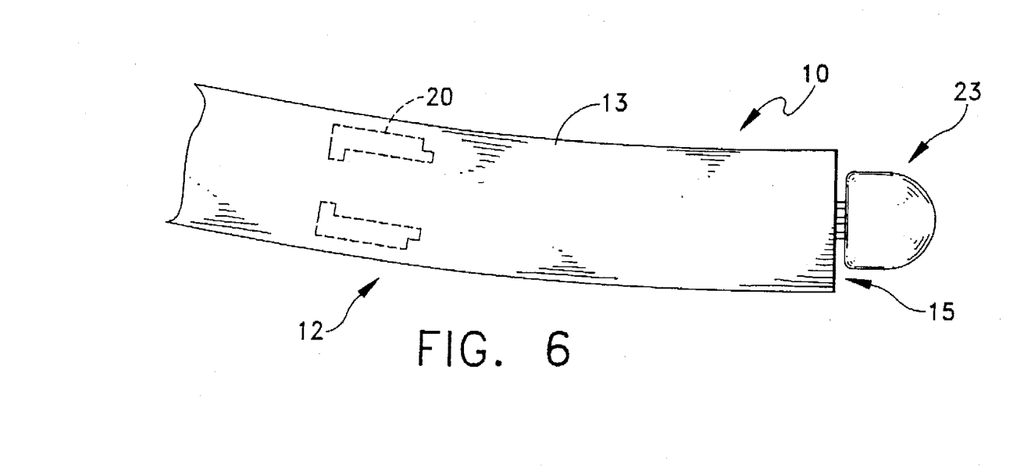
FIG. 6 is an enlarged plan view, partially in cross section, of a distal end of another delivery system incorporating another embodiment of this invention.

Referring now to FIG. 6, the outer tubular member 13 proximate the distal end 15 is depicted in a flexed position. The relatively short length of the metal segment 20 (depicted in phantom) enables such flexion of the portion of the member 13 therealong. Thus, those skilled in the art will now appreciate that the foregoing describes a delivery system comprising an axially extending, flexible tube structure housing that includes an impervious insert for shielding the tube structure from one or more abrading portions of a device positionable within the tube during transport and deployment within a patient's lumen. The relatively short axial length of the segment within the tube enables relative free radial flexion of the tube therealong. This embodiment also provides a delivery system that shields a flexible tube during deployment of a device having such an abrading surface and further provides that the delivery system after deployment of the device remains flexible along its length to facilitate the withdrawal of the system from a patient's lumen.

Figure 7:
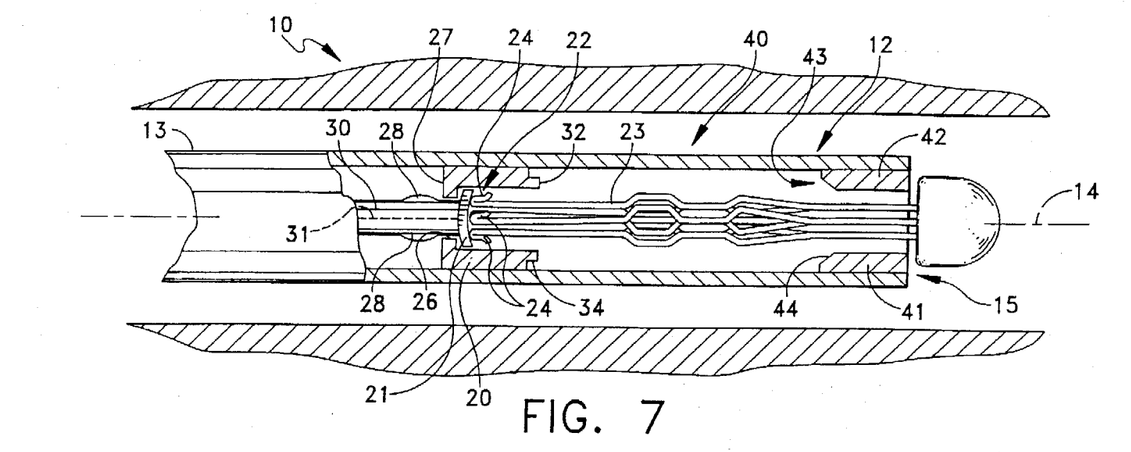
FIG. 7 is an enlarged plan view similar to FIG. 6 of still another embodiment of a delivery system according to this invention.

Referring now to FIG. 7 another delivery system 40 according to this invention that includes a distal end portion 12 similarly connected to a proximal end portion (not shown) as the embodiment of FIG. 2. In this instance, however, a stop 41 disposed at the distal end 15 comprises an second metal tube segment 42 secured to the outer tubular member 13. A proximal end 43 of the second metal segment 42 includes an inwardly tapered or chamfered surface 44 for engaging a leading edge 32 of the first metal segment 20. The leading edge or shoulder 32 comprises a reduced outer diameter section for engaging the second metal segment 42 along the chamfered portion 44. When the chamfered surface 44 of the proximal end 43 and the shoulder 32 engage, the outer tubular member 13 can still flex radially, because the metal segments 20 and 42 can displace relative to one another as can the corresponding elements in FIG. 6.

The delivery system 40 of FIG. 7 operates in substantially the same manner as the delivery system of FIG. 2. That is, the metal segment 20 moves initially distally, or to the right in FIG. 7 relative to the outer tubular member 13 upon actuation of a conventional control apparatus (not shown). The segment 20 moves distally until it engages a second, segment 42. Thereafter continued proximal displacement of the outer tubular member 13 relative to the inner member 17 urges both the metal segments 20 and 42 proximally so that the tabs 28 on the inner member 17 deflect or compress and urges the cup shaped member 21 distally through the metal segments 20 and 42 and out the distal end 15 of the outer tubular member 13. In this embodiment the hook portions 24 of the device 23 are shielded from the tubular member 13 by the metal segment 20 during transport of the device 23 to a delivery site in a patient's lumen and by the metal segments 20 and 42 during the relative retraction of the outer tubular member 13 that deploys the device 23.

It will be recognized that the inner surface of the segments 20 and 42 are both preferably smooth bored with the inner diameter of the segment 42 at its proximal end being at least as great as, if not greater than, the inner diameter of the segment 20 at the shoulder 34. This feature minimizes any tendency of the hook portions 24 to snag within or between the metal segments 20 and 42 as the device 23 moves distally during deployment thereof. Again, this structure assures substantial radial flexibility of the distal end portion 12 therealong both before and after the engagement of the segments 20 and 42 thereof. Thus, as depicted in FIG. 7, the distal end 32 of the metal segment 20 includes an outer portion of decreased diameter and the proximal end of segment 42 includes an inner tapered portion of increasing diameter having an increasing diameter per unit length greater than the decreasing diameter per unit length of the inner diameter of the metal segment 20. This relationship as well as other well known constructions will enable the relative radial deflection of such segments upon engagement.

Figure 8:
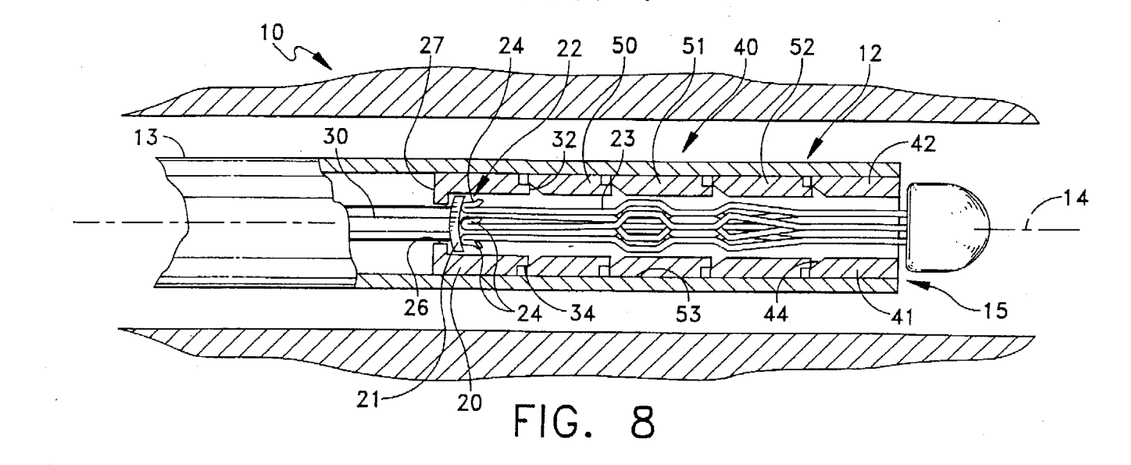
FIG. 8 is an enlarged plan view similar to FIG. 6 of yet another embodiment of a delivery system according to this invention.

Referring now to FIG. 8, the distal end 12 of the delivery system 10 includes in this instance the segments 20 and 42 with intermediate impervious metal segments 50, 51 and 52. A thin, flexible inner liner or sleeve 53 secures to and extends from the distal end 15 of the outer tubular member 13. The sleeve 53 and the outer tubular member 13 can be suitably joined by methods such as ultrasonic welding, adhesion bonding or rf welding. The sleeve 53 extends distally from the outer tubular member 13 and sheaths the segments 20, 42, 50, 51 and 52 therein. The hook portions 24 of the filter 23 reside within the confines of the segments during transport through a patient's lumens and during deployment prior to exiting through the distal end 15 of the outer tubular member 13.

In this embodiment, none of the segments 20, 42, 50, 51 and 52 significantly displace distally relative to the outer tubular member 13 upon actuation of the control apparatus to deploy the filter 23. Rather, in this case the segments 20, 42, 50, 51 and 52, which are essentially abutting adjacent segments, move proximally past the filter 23 with the outer tubular member 13. Thus, as will also be appreciated, the tabs 28 of the embodiment of FIG. 2 are not needed to control the displacement of the segment 20.

To enable the relative flexion of the distal end 15 of the tubular member 13, similar to that depicted in FIG. 6 with respect to the embodiment of FIG. 2, the distal and proximal ends of the segments 20 and 42 are formed with a shoulder and inner chamfered surface respectively as shown in FIG. 7. The distal and proximal ends of each of the metal segments 50, 51 and 52 are formed like the distal end 32 and of the segment 20 to proximal end 43 of the segment 42, respectively. Thus, each engagement or joint between proximal and distal ends of adjacent ones of the segments enable the passage of the abrading surface therealong and still enable radial displacement of the segments relative to each other.

Figure 9:
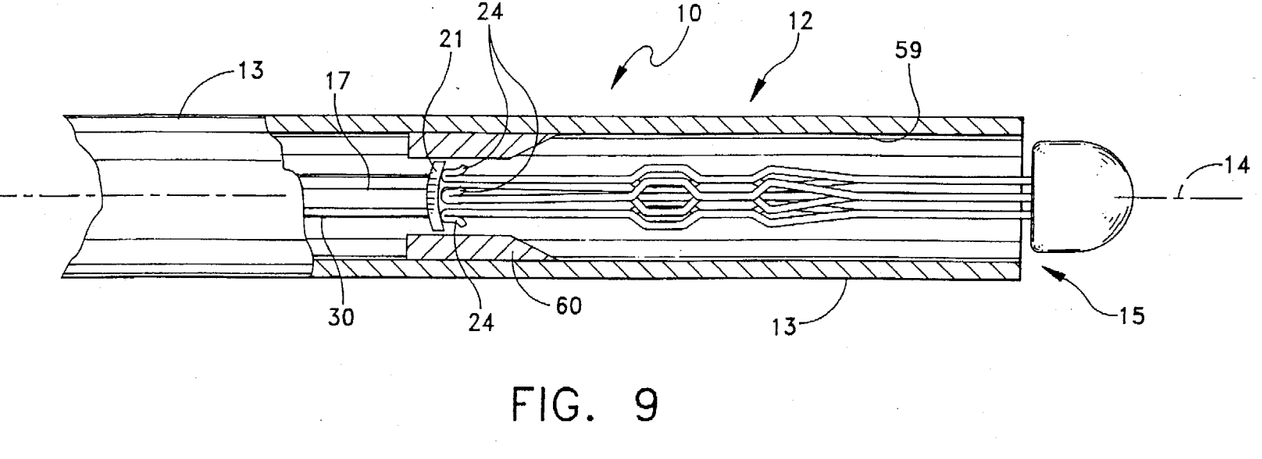
FIG. 9 is an enlarged plan view similar to FIG. 6 of yet still another embodiment of a delivery system according to this invention in an expanded form.

FIG. 9 depicts yet another embodiment of this invention includes the distal end 12 of the delivery system 10 with a metal tube segment 60. In this instance the metal segment 60 secures to the outer tubular member 13 proximally of the distal end 15 a distance corresponding to the distance between the distal end and the hook portions 24 of the device. The inner bore of the segment 60 is preferably smooth to enable relative free movement of the abrading portions 24 therealong during deployment of the filter 23. Actuation of the control apparatus (not shown) distally displaces the inner member 17 relative to both the outer member 13 and the tube segment 60. Thus, the filter 23 exits the tube segment 60 with the hook portions 24 contacting the inner wall of the tube prior to the exiting through the distal end 15.

Applicants have found that by forming the tube 13 of a relatively resilient, flexible polymer such as polypropylene or like material that the hook portions 24 of the filter 23 do not tend to penetrate or otherwise embed in the inner walls 59 during deployment of the filter 23 from the tube 13. However, the shielding device comprising the tube segment 60 interposed between the tube and the hook portions 24 prevents the abrading portions 24 from embedding in the walls of the tube 13 during delivery of the filter 23. Thus, the particular embodiment requires merely the securing of a small shield (segment 60) in the tubular member (13) proximally of the distal end to overlay the hook portions (24) of a device to be transported and then deployed by the system. The small nature of the segment 60 also enables relative transverse flexion of the tubular member therealong. Applicants prefer to form the segment 60 with the tapered distal end portion as depicted in FIG. 9, however it will be recognized and appreciated that many other configurations of the segment 60 are also appropriate. For example, the segment 60 can be formed with a blunt end without any taper.

Upon the relative distal retraction of the outer tubular member 13 relative to the inner member 17, the device 23 moves distally relative to the segment 60 with the hook portions 24 then contacting the inner surface (59) of the outer tubular member 13. Thus, due to the construction of the outer tubular member from a relatively resistance material such as polypropylene, the hook portions 24 do not embed or puncture the material as would more likely occur with polyester or polyethylene terephthalates tubing. Further, the segment hook portions 24 do not engage the surface of the tube during the transit of the delivery system through a patient's lumens of the outer tubular member 13 with the device 23 therein to the delivery site. As with the other embodiments of this invention, the segment 20 is relatively short so that the radial flexion of the tube 13 proximate the distal end 15 is not significantly impaired as depicted in FIG. 6 with respect to the embodiment of FIG. 2.

In summary, the foregoing describes several embodiments of a delivery system for transporting and deploying within a patient's lumen a device having an exposed abrading portion. The delivery system comprises an axially extending tubular member that is radially flexible, an impervious, relatively short shield portion for overlying the hook portion of the device during transport to a deployment site. The system also includes apparatus for urging the device distally with respect to the system to enable the deployment of the device within the patient's lumen. A system according to this invention may further include one or more additional shield members disposed between the distal end of the tubular member and the first shield portion such that the shield members are radially displaceable with respect to each other.

This invention has been disclosed in terms of certain embodiments. It will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. A method for delivery of self-expanding vena cava filter having a radially extending penetrating portion, said method comprising the steps of:

A) positioning an impervious, relatively short segment in a distal section of a radially flexible, axially stiff elongated tube, B) positioning the vena cava filter in the distal section of the tube with the segment interposed between the penetrating portions of the filter and the tube;

C) urging the distal section of the tube to a delivery site with a distal end of the tube positioned proximate the delivery site such that during said step of urging the distal section the distal end of the tube remains relatively radially flexible therealong with the segment overlying the penetrating portions; and D) urging the filter distally with respect to said tube to move the filter through an aperture in the distal end of the tube and thereby to deploy the filter at the delivery site.

2. A method as recited in claim 1 wherein said short segment constitutes a first segment, said method further comprising securing a second segment in the distal end of the tube wherein during said urging step the penetrating portions prior to passage through the aperture first engage the first segment and then said second segment.

3. A method as recited in claim 1 wherein said short segment constitutes a first segment, said method further comprising positioning a plurality of relatively short additional segments between the distal end and the first segment with a proximal end of each of the segments engaging a distal end of a proximally positioned segment, the engaging ends of the segments being formed to enable radial deflection between adjacent segments whereby the tubular member remains relatively radially flexible along the distal section in which the segments are positioned.

4. A method as recited in claim 3 wherein each of the segments respectively interpose between the penetrating portions and the tube as the filter moves distally in said tube.

5. A method as recited in claim 1 wherein said urging step urges the segment into engagement with a stop distally positioned in the tube relative such that the segment prior to engagement with the stop moves with the filter, the segment being interposed between the penetrating portion and the tube during said urging step prior to engaging the stop.

6. A delivery system for the percutaneous insertion of a self-expanding vena cava filter being formed with a length along a longitudinal filter axis, said system comprising an elongated, radially flexible and axially stiff tubular member extending proximally from a distal end and having a distal end section, a segment carried in said distal end section for constraining the filter in a compact condition substantially coaxially with said tubular member, said segment being relatively short compared to the axial length of the filter and having an inner surface that resists penetration by the filter thereby to protect said tubular member from damage during transport of the filter, and control means attached to said tubular member for displacing the filter from said segment thereby to deploy the filter.

7. A delivery system as recited in claim 6 wherein said segment comprises a tube segment coaxially supported within said tubular member.

8. A delivery system as recited in claim 7 wherein said tube segment is movably supported in said tubular member.

9. A delivery system as recited in claim 3 further including a stop positioned in said distal end wherein said control means connects with said tube segment to urge movement thereof and said stop limits the distal displacement of said tube segment.

10. A delivery system as recited in claim 9 wherein said tube segment releasably connects with said control means, actuation of said control means distally displacing said tube segment into engagement with said stop, continued actuation of said control means after the engagement of said stop and said tube segment releasing said tube segment from said control means and urging the displacement of the filter distally relative to both said distal end of said tubular member and said tube segment.

11. A delivery system as recited in claim 10 wherein said tube segment is a metal segment and said control means includes deflectable tabs that engage said metal segment and that deflect upon engagement of the tube segment with said stop, continued actuation of said control means after the engagement disengaging said metal segment from said control means.

12. A delivery system as recited in claim 9 wherein said tube segment constitutes a first tube segment and said stop comprises a second tube segment secured at said distal end of said tubular member.

13. A delivery system as recited in claim 12 wherein each of said first and second tube segments have a distal end section and a proximal end section and wherein said distal end section of said first tube segment has a reduced outer diameter for engaging said proximal end section of said second tube segment, said proximal end section having an enlarged inner diameter portion such that a portion of said proximal end section of said second tube segment overlies a portion of said distal end section of said first tube segment.

14. A delivery system as recited in claim 13 wherein each of said first and second tube segments has a relatively smooth internal bore thereby enabling relatively unencumbered distal displacement of the filter therethrough and wherein said distal end section of said first tube segment engages said proximal end section of said second tube segment in a manner enabling relative radial deflection between said first and second tube segments thereby enabling radial flexion of said distal end of said tubular member upon engagement of said first and second tube segments.

15. A delivery system as recited in claim 7 wherein said tube segment is formed of metal.

16. A delivery system as recited in claim 7 further including a stop positioned in said distal end of said tubular member wherein said tube segment is formed with a relatively smooth bore and said control means includes radially extending portions selectively engaging said tube segment to enable distal displacement of said tube segment relative to said tubular member during deployment of the filter and for selectively releasing said tube segment upon engagement of said tube segment with said stop to enable distal displacement of said device relative said tube segment.

17. A delivery system as recited in claim 7 wherein said tube segment constitutes a first tube segment, said system further comprising a second tube segment coaxially supported in said tubular member and distally positioned relative to said first tube segment, each of said first and second tube segments having a distal end section and proximal end section, respectively, formed to engage one another to enable radial deflection of said first tube segment relative to said second tube segment.

18. A delivery system as recited in claim 17 wherein said distal end section of said first tube segment has a reduced outer diameter and said proximal end section of said second tube segment has an enlarged inner diameter such that said proximal end section of said second tube segment is adapted to overlie a portion of said distal end section of said first tube segment.

19. A delivery system as recited in claim 18 further comprising at least one additional tube segment coaxially supported in said tubular member intermediate said first and second tube segments, each said additional tube segment including proximal and distal end sections corresponding to said proximal end section of said first tube segment and said distal end section of said second tube segment, respectively whereby each of said first, second and additional tube segments is radially deflectable relative to any adjacent tube segment.

20. A delivery system as recited in claim 7 wherein said tube segment constitutes a first tube segment, said system further comprising at least one additional tube segment disposed distally of said first tube segment in said tubular member.

21. A delivery system as recited in claim 20 wherein each of said tube segments are radially deflectable relative to adjacent ones of said tube segments.

22. A delivery system as recited in claim 20 wherein said system includes at least two additional tube segments each having distal and proximal end sections and extending distally of said first tube segment and wherein said distal end section of each of said tube segments intermediate a distal most tube segment and said first tube segment abuts a proximal end section of another of said additional tube segments having a reduced outer diameter and each of said proximal end sections of said tube segments intermediate a distal most tube segment and said first tube segment has an enlarged inner diameter such that the proximal section of one of said tube segments overlies a portion of said reduced outer diameter distal section of any adjacent tube segment.

23. A delivery system for delivering to a delivery site in a compact form a self-expansible vena cava filter with exposed penetrating surfaces and for selectively deploying the filter at the delivery site, said system comprising:

A) catheter means extending proximally along an axis from a proximal end to a distal end of said system, said catheter means positioning said distal end at the delivery site, said catheter means being radially flexible and having an internal lumen with a lumen surface for receiving and housing the filter proximate said distal end for transport to and deployment at the delivery site;

B) retaining means in said internal lumen of said catheter means for overlying the penetrating surfaces of the filter thereby to shield said catheter means from the exposed penetrating surfaces and for enabling a radial flexion of said catheter means therealong during transport of the filter by said delivery system, said retaining means including a tubular metal segment coaxially positioned in said internal lumen of said catheter means and interposed between said lumen surface of said catheter means and the penetrating portions of the filter during transport thereof through the patient's lumen; and C) control means extending from a proximal end of the system through said catheter means to said retaining means for selectively deploying the device.

24. A delivery system as recited in claim 23 further comprising a stop in said lumen at said distal end of said catheter means and said control means connects with said retaining means such that said stop limits the distal travel of said retaining means in said lumen.

25. A delivery system as recited in claim 23 wherein said control means includes a handle disposed at said proximal end of said system supporting said catheter means, manual manipulation means connected to said handle for urging the filter distally relative to said catheter means to enable selective deployment of the filter, and an axially stiff inner member extending distally through said lumen and for contacting a proximal end of the filter such that actuation of said manipulation means urges said inner member distally relative to said catheter means to urge the proximal end of the filter distally through said lumen.

26. A delivery system as recited in claim 25 wherein said retaining means includes a plurality of tubular segments disposed axially in said lumen with the most proximal tubular segment overlying the penetrating surfaces of the filter and positioned in said lumen for transport of the filter, the most distal tubular segment being secured to said catheter means at said distal end.

27. A delivery system as recited in claim 26 wherein each tubular segment has a distal end and a proximal end, wherein each distal end of said plurality of tubular segments opposite a proximal end of another of said tubular segments has a reduced outer diameter, wherein each proximal end of said tubular segment adjacent said distal end of a tubular segment has an enlarged inner diameter such that the proximal end of one of said tubular segments overlies the distal end of an adjacent one of said tubular segments.

28. A delivery system as recited in claim 27 wherein said plurality of tubular segments consists of first and second tubular segments with said first tubular segment during transport of the filter being spaced from said second tubular segment, said first tubular segment being releasably connected to said control means such that upon actuation of said control means said first tubular segment and the filter move distally relative to said second tubular segment in said catheter means such that said first tubular segment, upon engagement with said second tubular segment and continued actuation of said control means, releases from said control means.

29. A delivery system as recited in claim 27 wherein said plurality of tubular segments include intermediate tubular segments disposed between most distal and most proximal tubular segments with each of said intermediate tubular segments engaging at least one adjacent tubular segment.

30. A delivery system as recited in claim 25 wherein said catheter means is formed of a polypropylene-type material and said retaining means comprises an impervious short tubular segment disposed in said internal lumen to overlie the penetrating surfaces of the filter during transport thereof in said internal lumen, said tubular segment being secured in said internal lumen.

* * * * *